United States Patent [19]

Lippmann

[11] 4,118,493

[45] Oct. 3, 1978

[54] METHOD OF TREATING HYPERCHLORHYDRIA AND/OR ASSOCIATED CONDITIONS WITH 1,3-DIOXO-1H-BENZ(DE)ISOQUINOLINE-2-(3H)-ACETIC ACID

[75] Inventor: Wilbur Lippmann, Montreal, Canada

[73] Assignee: American Home Products Corporation, New York, N.Y.

[21] Appl. No.: 818,378

[22] Filed: Jul. 25, 1977

[51] Int. Cl.$^2$ ............................................. A61K 31/47
[52] U.S. Cl. .................................................... 424/258
[58] Field of Search ....................................... 424/258

[56] References Cited

U.S. PATENT DOCUMENTS 3,821,383   6/1974   Sestanj et al. ...................... 424/258

*Primary Examiner*—Frederick E. Waddell
*Attorney, Agent, or Firm*—Adley F. Mandel

[57] ABSTRACT

A method is disclosed for preventing the secretion of excessive amounts of hydrochloric acid in the stomach of humans suffering from hyperchlorhydria and/or associated conditions by administering an effective amount of 1,3-dioxo-1H-benz[de]isoquinoline-2(3H)-acetic acid.

4 Claims, No Drawings

METHOD OF TREATING HYPERCHLORHYDRIA AND/OR ASSOCIATED CONDITIONS WITH 1,3-DIOXO-1H-BENZ(DE)ISOQUINOLINE-2-(3H)-ACETIC ACID

BACKGROUND OF THE INVENTION (a) Field of Invention

This invention relates to a method for preventing the secretion of excessive amounts of hydrochloric acid in the stomach of humans suffering from hyperchlorhydria and/or associated conditions. Since the usual peptic ulcer is frequently accompanied by, or the result of, hyperchlorhydria, my method is especially useful in the treatment of peptic ulcers and associated abnormal conditions of the gastrointestinal tract.

(b) Prior Art

The active agent of this invention, 1,3-dioxo-1H-benz-[de]isoquinoline-2(3H)-acetic acid, or a therapeutically acceptable salt thereof, is disclosed in U.S. Pat. No. 3,821,383, issued June 28, 1974. This active agent, hereinafter sometimes designated as "alrestatin", previously has been reported to be useful in preventing or relieving diabetic complications such as cataracts, neuropathy, nephropathy and retinopathy (see U.S. Pat. No. 3,821,383). I have now found unexpectedly that alrestatin, either in its free acid form or in its therapeutically acceptable salt form, is an inhibitor of gastric acid secretion and ulcer formation.

This finding, coupled with the fact that alrestatin is a relatively safe drug, renders the method of this invention particularly useful and advantageous.

SUMMARY OF THE INVENTION

According to this invention a method is provided for preventing the secretion of excessive amounts of hydrochloric acid in the stomach of humans, which comprises administering to a human suffering from hyperchlorhydria and/or associated conditions an effective amount of 1,3-dioxo-1H-benz[de]isoquinoline-2(3H)-acetic acid, or a therapeutically acceptable salt thereof.

DETAILS OF THE INVENTION

According to the present method, alrestatin, either in its free acid form or in the therapeutically acceptable salt form is employed as the active agent. Examples of suitable salt forms are described in U.S. Pat. No. 3,821,383 and include the sodium, potassium, magnesium, triethylamine and benzylamine salt forms. A preferred salt form is the sodium salt, i.e. alrestatin sodium.

Alrestatin or a therapeutically acceptable addition salt thereof is administered to humans suffering from hyperchlorhydria or associated conditions for the purpose of preventing secretion of excessive amounts of the hydrochloric acid in the stomach and gastrointestinal tract thereof, either orally or parenterally. For many reasons oral administration is preferred.

While alrestatin or a therapeutically acceptable salt thereof can be administered alone, e.g. as a sole component of a filled capsule, it is preferred to formulate the compound in various dosage forms for oral or parenteral administration, e.g. tablets, or sterile solutions. Such formulations are described in U.S. Pat. No. 3,821,383, herein incorporated by reference.

When ultilizing alrestatin or one of its above-noted salts as agents for combating or preventing hyperchlorhydria, and/or associated conditions, the total dose of active agent can range from 1.0 to 1,000 mg per kilogram of body weight per day with a preferred dosage range of from 50 to 500 mg per kilogram of body weight per day. Generally, a parenteral dose or an oral dose is administered in two to four applications per day. Such doses are considered to be effective amounts when, following their administration, either the amounts of hydrochloric acid secreted within a specified period of time by the human being so treated are significantly reduced, or when the subjective symptoms complained of by said human beings are reported as having disappeared, or being ameliorated or reduced in severity following such treatment.

The effectiveness of alrestatin or its therapeutically acceptable salts as agents for preventing hyperchlorhydria and inhibiting hydrochloric acid secretion is demonstrated by the use of rats, more especially the Shay rat. The rat is the preferred experimental mammal for demonstrating the activity of agents affecting gastric acid secretion and it has been widely used in experimental medicine for this purpose. For instance, on page 149 in "Pathophysiology of Peptic Ulcer", published by McGill University Press, Montreal, Canada in 1963, Skoryna states that many of the drugs now in use in human medicine for the treatment of peptic ulcer have been evaluated by the Shay rat method. It is recognized by skilled pharmacologists that results obtained in the Shay rat in the evaluation of gastric acid conditions are translatable to results that will be obtained when the same drug is administered to human beings. For the value of the Shay rat in experimental gastroenterology, see also the article by H. Shay et al., Gastroenterology, 26, 906 (1954). This animal is generally recognized as the preferred, or standard, animal for use experimentally in testing drugs used to inhibit gastric acid secretion.

More specifically, the effect of alrestatin sodium on gastric acid secretion was measured essentially according to the method of H. Shay et al., Gastroenterology, 26, 906 (1954) as described by Lippmann, J. Pharm. Pharmacol., 22, 568 (1970). Rats (female albino Sprague Dawley, Canadian Breeding Laboratories; 165–190 g) were fasted for 48 hours before pyloric ligation. After the first 24 hours of fasting the animals were given access to 8% sucrose in 0.2% sodium chloride for eight hours. Water was permitted ad libitum except during the eight hours access to sucrose and after the test compound treatment. The test compound was administered orally by gavage one hour before the ligation of the pylorus or intraperitoneally immediately after the ligation. The vehicle employed was water containing one drop of polysorbate 80 per 7 ml; 0.2 ml was administered p.o. and 0.5 ml i.p. (Polysorbate 80 is a mixture of sorbitol and its anhydrides copolymerized with ethylene oxide.) The pylorus was ligated under diethyl ether anesthesia and the sutured incision was covered with flexible collodion to prevent the animals from ingesting adhering blood. The stomachs were lavaged with 0.9% sodium chloride until the return solution was clear. Four hours after pyloric ligation, the animals (15–18 per group) were killed with diethyl ether and the gastric contents were collected in centrifuge tubes. The amount of acid in the centrifuged gastric juice was determined by titration against 0.1 N sodium hydroxide in a direct reading pH meter to pH 7.0.

Alrestatin sodium administered intraperitoneally (22–200 mg/kg), immediately after pyloric ligation, inhibited the gastric acid secretion. The gastric acid secretion was decreased in a linear dose-response manner with the dose causing a 50% inhibition, i.e. $ED_{50}$, being 90 mg/kg. The volume of gastric juice produced also was decreased in a linear dose-response manner.

Alrestatin sodium also was effective when administered orally (22–200 mg/kg), one hour before pyloric ligation, in inhibiting the gastric acid secretion with the $ED_{50}$ being 180 mg/kg. The volume of gastric juice produced was also decreased. The free acid also is effective.

Again, more specifically, the ability of alrestatin sodium to inhibit the secretion of hydrochloric acid and prevent ulcer formation can be demonstrated experimentally; for instance, by determining its effect on ulcer formation in the non-glandular portion of the stomach induced by pyloric ligation according to the method of H. Shay et al., Gastroenterology, 5, 43 (1945) as described by Lippmann and Seethaler, Experientia, 29, 993 (1973). Rats (female, 165–190 g) caged individually were fasted, as described above, and pylorus-ligated under diethyl ether anesthesia. Alrestatin sodium (0.8 ml, p.o.; 0.5 ml, i.p.) or saline was administered immediately after pyloric ligation and the animals were sacrificed 19 hours later. There were seven to thirteen animals per group.

Alrestatin sodium given intraperitoneally (200–800 mg/kg), immediately after the pyloric ligation, antagonized the induced ulcer formation with the $ED_{50}$ being 330 mg/kg. Alrestatin sodium administered orally (200–800 mg/kg), one hour before the pyloric ligation, exhibited an $ED_{50}$ of 500 mg/kg for the antiulcer activity.

The present findings demonstrate that alrestatin is an effective inhibitor of gastric acid secretion and ulcer formation in the rat. Alrestatin is well-absorbed as it was about one-half as effective when administered orally in comparision to intraperitoneally. In addition to acting to cause a decrease in gastric acid output, alrestatin also acts to decrease the volume of gastric juice.

Furthermore, alrestatin does not exhibit appreciable antichlolinergic activity in vitro or in vivo. Thus, it does not act in the manner of known anticholinergic agents, e.g. atropine, when they are used as gastric acid antisecretory and antiulcer agents. Accordingly, the side effects associated with the use of the latter agents, e.g. dry mouth, blurred vision, palpitation, etc., see D. W. Piper et al., Drugs 10, 56 (1975), are avoided by the employment of the present method.

Finally, the $LD_{50}$ of alrestatin in rats according to the route of administration is greater than 2,500 mg/kg (perorally); 1220 ± 45 mg/kg (intravenously); and 1380 ± 80 mg/kg (intraperitoneally). Therefore, a good therapeutic index of safety is present.

I Claim:

1. A method for preventing the secretion of excessive amounts of hydrochloric acid in the stomach of humans, which comprises: administering to a human suffering from hyperchlorhydria an effective amount of 1,3-dioxo-1H-benz[de]isoquinoline-2(3H)-acetic acid, or a therapeutically acceptable salt thereof.

2. The method of claim 1 in which the effective amount is within the range of from 1.0 to 1,000 mg per kilogram of body weight.

3. The method of claim 1 in which the effective amount is within the range of 50 to 500 mg per kilogram of body weight.

4. The method of claim 1 in which the therapeutically acceptable salt is the sodium salt.